United States Patent [19]

Zurita

[11] Patent Number: 4,676,745
[45] Date of Patent: Jun. 30, 1987

[54] ORTHODONTIC APPLIANCE

[76] Inventor: Victor M. Zurita, 3803 Central Rd., Rolling Meadows, Ill. 60008

[21] Appl. No.: 756,163

[22] Filed: Jul. 18, 1985

[51] Int. Cl.⁴ .............................................. A61C 3/00
[52] U.S. Cl. ......................................... 433/6; 433/7; 433/18; 433/21
[58] Field of Search .................... 433/6, 7, 18, 19, 21, 433/24

[56] References Cited

U.S. PATENT DOCUMENTS

| | | | |
|---|---|---|---|
| 1,044,764 | 11/1912 | Federspiel | 433/18 |
| 1,773,588 | 8/1930 | Linde | 433/7 |
| 2,318,001 | 5/1943 | Linde | 433/10 |
| 2,789,351 | 4/1957 | Gordon | 433/6 |
| 3,162,948 | 12/1964 | Gerber | 433/7 |
| 3,510,946 | 5/1970 | Kesling | 433/6 |
| 3,898,736 | 8/1975 | Bergersen | 433/6 |
| 4,026,023 | 5/1977 | Fisher | 433/7 |
| 4,091,540 | 5/1978 | Wallshein | 433/21 |
| 4,167,061 | 9/1979 | Forster | 433/5 |
| 4,224,021 | 9/1980 | Foxman | 433/6 |
| 4,231,736 | 11/1980 | Reilly | 433/6 |
| 4,272,240 | 6/1981 | Glassman | 433/18 |
| 4,347,054 | 8/1981 | Kraus et al. | 433/7 |
| 4,354,832 | 10/1982 | Wallshein | 433/7 |
| 4,373,913 | 2/1983 | McAndrew | 433/7 |
| 4,413,978 | 11/1983 | Kurz | 433/6 |
| 4,468,196 | 8/1984 | Keller | 433/7 |
| 4,571,178 | 2/1986 | Rosenberg | 433/7 |

FOREIGN PATENT DOCUMENTS 0247459  10/1963  Australia .............................. 433/18

Primary Examiner—John J. Wilson
Assistant Examiner—Adriene J. Lepiane
Attorney, Agent, or Firm—Wood, Dalton, Phillips, Mason & Rowe

[57] ABSTRACT

An orthodontic appliance to establish and maintain normal alignment of the teeth. The orthodontic appliance includes a U-shaped band of flexible material having a pair of rearwardly extending arms where the U-shaped band conforms to the labial surface of the dental arch when in position in the mouth. It also includes a pair of anchors each of which is adapted to cooperate with a molar on opposite sides of the mouth to maintain the U-shaped band in position against the labial surface of the dental arch. The orthodontic appliance further includes a resilient member joining the anchors to the arms of the U-shaped band with the resilient member applying a biasing force to the labial surface of the dental arch through the U-shaped band. In addition, the orthodontic appliance may include a U-shaped member releasably securable to the anchors for applying a counterforce to the front teeth of the dental arch.

25 Claims, 9 Drawing Figures

U.S. Patent  Jun. 30, 1987  4,676,745
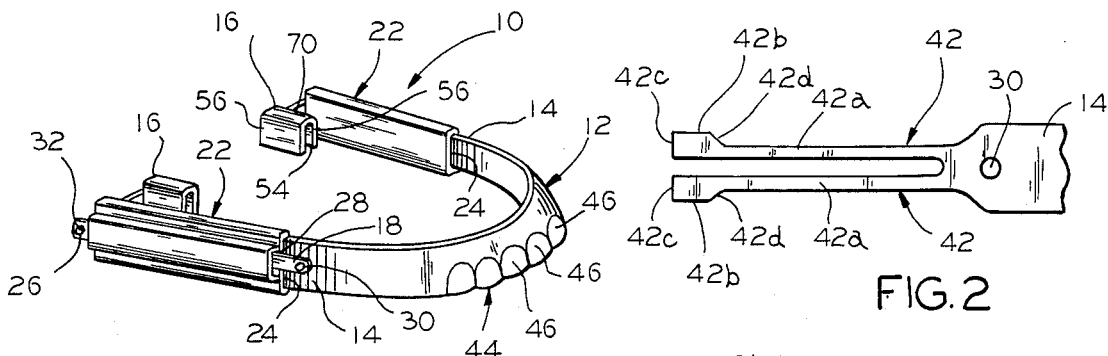
FIG.1
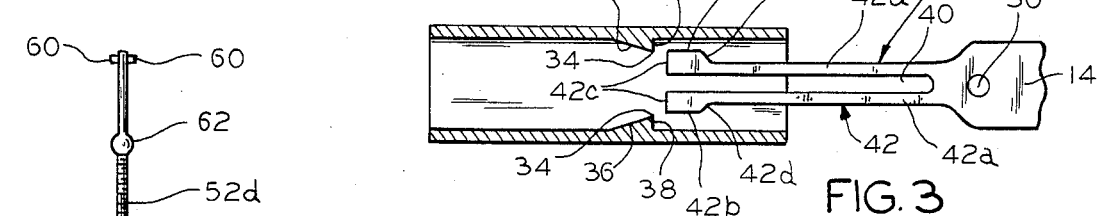
FIG.2
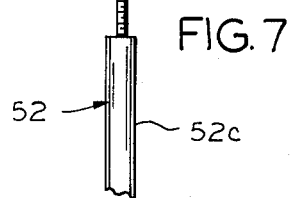
FIG.7
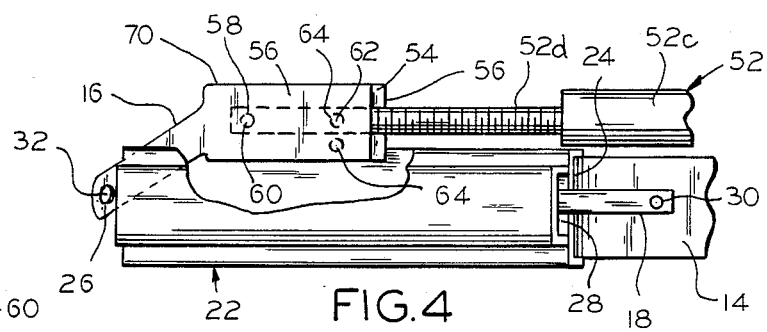
FIG.3
FIG.4
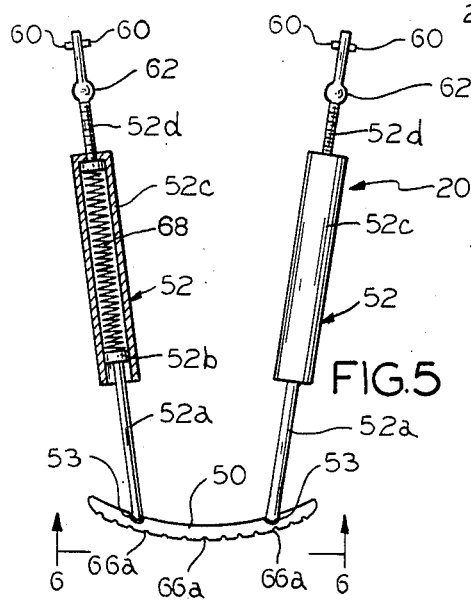
FIG.5
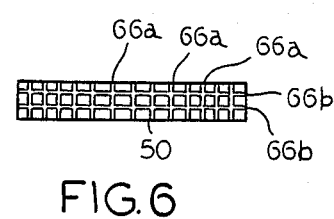
FIG.6
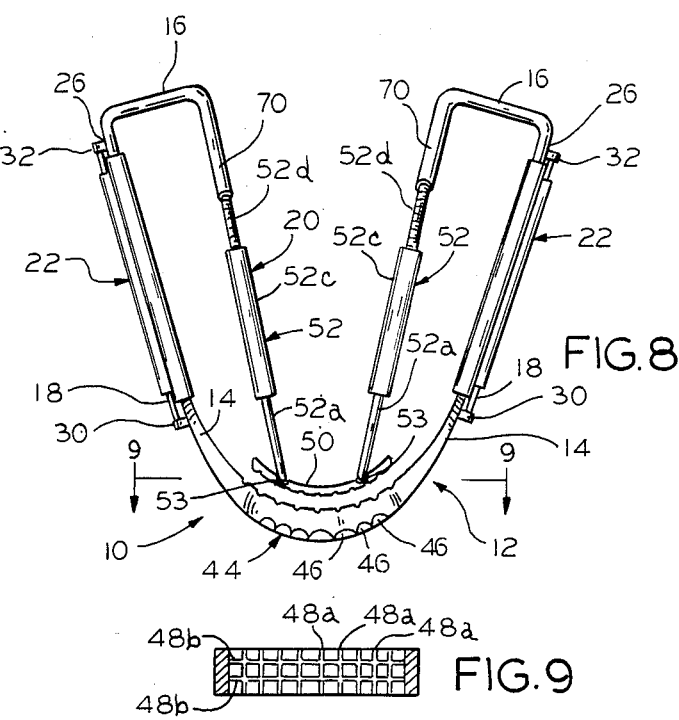
FIG.8
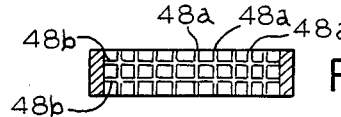
FIG.9

ORTHODONTIC APPLIANCE

BACKGROUND OF THE INVENTION

The present invention relates to orthodontic appliances and, more particularly, to an orthodontic appliance for establishing and maintaining normal alignment of the teeth.

In straigtening teeth, it is common practice to employ metal bands looped about groups of teeth and about selected individual teeth to exert a steady force. This force is utilized to slowly pull the teeth into alignment over a protracted period of time and with periodic adjustment of band tension and location. While usually effective, and required for advanced cases of deformity of the dental arch, such devices are unduly complex in structure and unnecessarily expensive to install and adjust in less severe cases.

Moreover, it is now well recognized that, particularly in children, the teeth slowly deviate from normal alignment over a relatively long period of time. This phenomena suggests the desirability of a temporary brace to maintain normal alignment during the formative years, particularly of the front teeth of growing children, in order to avoid the necessity of the more costly and complex orthodontic appliances utilized for advanced degrees of deformity. Unfortunately, there has been a noticeable lack of acceptable devices for this purpose.

Additionally, where there is incipient deviation in growing children, normal orthodontic appliances are oftentimes unnecessary to reestablish normal alignment. Once again, the usual method employing metal bands is far more than is required and difficult, if not impossible, to justify due to the cost and potential discomfort to the child. Even in the case of adults, unless an advanced degree of deformity exists, a simple, inexpensive orthodontic appliance could be utilized.

Unfortunately, despite the clear need for such devices, there has been no known temporary brace available to satisfy the demand. This can be explained, in part, by the misconception of the public that, even for incipient deviation, there is no alternative but to turn to complex appliances installed and adjusted by orthodontists at considerable expense. However, in large part, there has been no suitable orthodontic appliance available to satisfy the demand for a temporary brace.

The present invention is directed to overcoming the above stated problems and accomplishing the stated objectives.

SUMMARY OF THE INVENTION

Accordingly, the present invention is directed to an orthodontic appliance capable of establishing and maintaining normal alignment of the teeth. The orthodontic appliance includes a U-shaped band of flexible material having a pair of rearwardly extending arms and conforming to the labial surface of the dental arch when in position in the mouth. It also includes anchor means adapted to cooperate with a molar on each side of the mouth to maintain the U-shaped band in position against the labial surface of the dental arch. The orthodontic appliance further includes resilient means joining the anchor means to the arms of the U-shaped band and applying a biasing force to the labial surface of the dental arch through the U-shaped band. With this arrangement, the biasing force can be determined by the strength of the resilient means.

In an exemplary embodiment, the anchor means includes a pair of U-shaped hooks each facing opposite the U-shaped band and being operatively associated with one of the arms on opposite sides of the U-shaped band. One of the U-shaped hooks is preferably adapted to engage a molar on each side of the mouth. Also, the anchor means includes a pair of elongated slide members each having its rearwardmost end connected to one of the U-shaped hooks and having a hollow channel adapted to telescopically receive and guide one of the arms of the U-shaped band.

Further, the resilient means preferably comprises a pair of elongated biasing members with one of the biasing members being associated with each of the arms of the U-shaped band. The biasing members extend from a point adjacent the rearwardmost end of the corresponding one of the slide members to a point on the corresponding arm forward of the slide member. As a result, the biasing members apply a force tending to telescope the arms of the U-shaped band further into the slide members when in position in the mouth.

In addition, the elongated slide members preferably each include a second hollow channel extending parallel to the arm-receiving hollow channel. The second hollow channels are substantially aligned with connection means for the biasing members associated with the arms and the anchor means, and the biasing members extend through the second hollow channels of the elongated slide members. In particular, the connection means preferably includes a corresponding pair of studs on each of the arms and anchor means, and the biasing members preferably comprise elastic bands joining the corresponding pairs of studs.

In a preferred embodiment, the elongated slide members each include a pair of inwardly directed protrusions defined by forwardly and inwardly ramped surfaces terminating in forwardly facing vertical surfaces. The rearwardly extending arms each are advantageously split lengthwise to define a pair of secondary arms adapted to be disposed in locked position against the forwardly facing vertical surfaces during placement of the appliance in the mouth. Also, the secondary arms are adapted to be forced together to be moved rearwardly of the inwardly directed protrusions after the U-shaped hooks have been placed in engagement with a molar on each side of the mouth.

When there is more complex deformity of the front teeth, such as vertical rotation around their axes or backward displacement, the orthodontic appliance can include means for applying a counterforce to the front teeth of the dental arch. The counterforce applying means is preferably releasably securable to the anchor means and comprises a generally U-shaped member adapted to fit within the U-shaped band. Specifically, the U-shaped member preferably has a curved surface adapted to engage the posterior surface of the front teeth and a pair of connecting arms extend rearwardly from the curved surface to the anchor means.

With this construction, the connecting arms are adapted to be releasably secured to the anchor means. When so connected, the connecting arms also each include intermediate biasing means comprising a first arm portion having a plunger disposed in one end of a spring loaded cylinder and a second arm portion threaded into the other end of the cylinder. As a result, the connecting arms are adapted to bias the U-shaped member outwardly to provide the counterforce.

Other objects and advantages of the present invention will become apparent from the following specification taken in conjunction with the accompanying drawings.

DESCRIPTION OF THE DRAWINGS

FIG. 1 is a perspective view of an orthodontic appliance in accordance with the present invention;

FIG. 2 is an elevational view of a rearwardly extending arm of the U-shaped band of the orthodontic appliance of FIG. 1;

FIG. 3 is a view similar to FIG. 2 illustrating insertion of the rearwardly extending arm into an elongated slide member;

FIG. 4 is an elevational view of the posterior portion of the orthodontic appliance of FIG. 1 with a counterforce applying member secured thereto;

FIG. 5 is a top plan view, partially in section, of the counterforce applying member for use with the orthodontic appliance of FIG. 1;

FIG. 6 is a front elevational view of the counterforce applying member taken on the line 6—6 of FIG. 5;

FIG. 7 is a top plan view of a connecting arm of the counterforce applying member illustrated in FIG. 5;

FIG. 8 is a top plan view of the orthodontic appliance with the counterforce applying member secured thereto; and FIG. 9 is a rear elevational view of the orthodontic appliance taken on the line 9—9 of FIG. 8.

DESCRIPTION OF THE PREFERRED EMBODIMENTS

An exemplary embodiment of an orthodontic appliance for establishing and maintaining normal alignment of the teeth in accordance with the invention is illustrated in FIG. 1. The orthodontic appliance 10 includes a U-shaped band 12 of flexible material having a pair of rearwardly extending arms 14 and conforming to the labial surface of the dental arch when in position in the mouth. It also includes anchor means, such as the U-shaped hooks 16, adapted to cooperate with a molar on each side of the mouth to maintain the U-shaped band 12 in position against the labial surface of the dental arch. The orthodontic appliance 10 further includes resilient means, such as the elastic bands 18, joining the U-shaped hooks 16 to the arms 14 of the U-shaped band 12 and applying a biasing force to the labial surface of the dental arch through the U-shaped band. In addition, in a preferred embodiment, the orthodontic appliance 10 may include means for applying a counterforce to the front teeth of the dental arch, such as the U-shaped member 20, releasably securable to the U-shaped hooks 16 (see FIGS. 5 and 8).

Referring to FIG. 8, the U-shaped hooks 16 each face opposite the U-shaped band 12 and are operatively associated with one of the arms 14 on opposite sides of the U-shaped band 12. One of the U-shaped hooks 16 is adapted to engage a molar on each side of the mouth. In addition, the anchor means also preferably includes a pair of elongated slide members 22 each having a hollow channel 24 adapted to telescopically receive and guide one of the arms 14 of the U-shaped band 12.

Further, the U-shaped hooks 16 each are connected to the rearwardmost end of one of the elongated slide members 22 by a joint 26 accommodating relative pivotal movement of the U-shaped hooks 16 relative to the slide members 22. With this construction, the relative pivotal movement permits the U-shaped hooks 16 to be positioned so as to comfortably and securely engage a molar on each side of the mouth.

As previously mentioned, the resilient means comprises a pair of elongated biasing members in the form of elastic bands 18. One of the elastic bands 18 is associated with each of the arms 14 of the U-shaped band 12 and extends from a point adjacent the rearwardmost end of the corresponding one of the slide members 22 to a point on the corresponding arm 14 forward of the slide member 22. It will be appreciated that the elastic bands 18 thereby apply a force tending to telescope the arms 14 further into the slide members 22. The elongated slide members 22 also each include a second hollow channel 28 extending parallel to the corresponding arm-receiving hollow channel 24 substantially aligned with connection means for the elastic band 18 associated with the corresponding arm 14 and U-shaped hook 16. With this construction, the elastic bands 18 extend through the second hollow channels 28 of the elongated slide members 22 and, with the connection means including corresponding pairs of studs 30 and 32 on the arms 14 and U-shaped hooks 16, the elastic bands 18 join the corresponding pairs of studs, as shown in FIGS. 1, 4 and 8.

Referring to FIG. 3, the elongated slide members 22 each include a pair of inwardly directed protrusions 34 defined by forwardly and inwardly ramped surfaces 36 terminating in forwardly facing vertical surfaces 38. The rearwardly extending arms 14 are each split lengthwise, as at 40, to define a pair of secondary arms 42 adapted to be disposed in locked position against the forwardly facing vertical surfaces 38 during placement of the appliance 10 in the mouth. Moreover, the secondary arms 14 are adapted to be forced together for insertion past the protrusions 34 after the U-shaped hooks 16 have been placed in engagement with a molar on each side of the mouth.

Referring to FIGS. 2 and 3, the secondary arms 42 each include a narrow elongated portion 42a terminating in an enlarged end 42b. The enlarged ends 42b each include a rearwardly facing vertical surface 42c adapted to be disposed in engagement with one of the forwardly facing vertical surfaces 38 of the inwardly directed protrusions 34 of the slide members 22. Moreover, the enlarged ends 42b also each include a curved surface 42d adapted to cooperate with one of the forwardly and inwardly ramped surfaces 36 of the slide members 22.

Preferably, the U-shaped band 12 is formed of plastic. It may also be formed with an embossment, as at 44 simulating teeth 46 on the outer surface thereof and may include a plurality of vertical grooves or ribs 48a and/or a plurality of horizontal grooves or ribs 48b (see FIGS. 8 and 9) or any other means to grip the teeth on the inner surface thereof. By utilizing a plastic with flexibility characteristics, the arms 14 are movable toward one another for insertion of the appliance 10 into the mouth.

As previously mentioned, the counterforce applying means is a generally U-shaped member 20 adapted to fit within the U-shaped band 12 (see FIG. 8). The U-shaped member 20 has a curved surface 50 adapted to engage the posterior surface of the front teeth and a pair of connecting arms 52 extending therefrom and connected thereto by means of the ball and socket joints 53. As shown in FIG. 4, the connecting arms 52 are adapted to be releasably secured to the U-shaped members 16.

In particular, the connecting arms 52 each include intermediate biasing means such as a first arm portion 52a having a plunger 52b disposed in one end of a spring-loaded cylinder 52c and a second arm portion 52d threaded into the other end of the spring-loaded cylinder 52c. The connecting arms 52, so formed, bias the U-shaped member and, in particular, the curved surface 50, outwardly to provide the counterforce. Moreover, the connecting arms 52 are received in forwardly facing cavities 54 in each of the U-shaped hooks 16 defined by a pair of generally parallel walls 56.

As shown in FIGS. 4 and 5, the connecting arms 52 and walls 56 have mutually interengageable connection means including a pair of aligned stud receiving holes such as 58 in each of the pairs of walls 56 defining the cavities 54. The connecting arms 52 each have a corresponding pair of oppositely facing studs 60 adapted to be releasably disposed in the holes 58 such that the U-shaped member 20 is pivotable about the studs 60. Additionally, the connection means includes detent means associated with the walls 54 and the connecting arms 52 accommodating retention of the U-shaped member 20 in positions of angular adjustment relative to the studs 60. The detent means includes a detent 62 on each of the connecting arms 52 forwardly of the studs 60 and at least two generally vertically aligned detent receiving indentations 64 forwardly of the holes 58 in each of the pairs of walls 56 defining the cavities 54. With this arrangement, the U-shaped member 20 can be pivoted about the stud 60 into the most advantageous position for applying a counterforce.

As will be appreciated, the simulated front teeth 46 make wearing the device less obvious. In addition, the U-shaped band 12 can otherwise be formed of clear plastic and, with the grooves 48 in the rear surface of the U-shaped band 12, the band provides improved adhesion to the teeth even though the material of the band is thin and flexible for insertion into the mouth. In other words, the thin, flexible nature of the U-shaped band 12 enables it to be narrowed by squeezing for introduction into the mouth.

With regard to the U-shaped hooks 16 and the elongated slide members 22, they can advantageously be formed of a light metallic material with each being a mirror image of the other. The metallic material, if desired, can be plastic coated for comfort in the mouth. In any event, the U-shaped hooks 16 should be formed of sufficiently flexible or malleable metal to releasably secure the U-shaped member 20.

As mentioned above, the elongated biasing members are preferably in the form of elongated elastic bands 18 although it is also possible to utilize springs for this same purpose. In either case, the bands or springs will extend through the hollow channels 28 in the elongated slide members 22 for attachment to the studs 30 and 32.

Preferably, the U-shaped hooks 16 are designed to embrace the posterior part of the last molar on each side of the mouth. The U-shaped hooks 16 are also preferably connected to the elongated slide members 22 by means of short, snug rivet-like joints which are provided by means of the studs 32. With this arrangement, the joints accommodate relative pivotal movement between the U-shaped hooks 16 and the elongated slide members 22 for a better fit.

As previously mentioned, the secondary arms 42 include thin, flexible portions 42a. The enlarged ends 42b of the portions 42a will stop insertion of the secondary arms 42 when contacting the forwardly facing vertical surfaces 38 within the elongated slide members 22 unless the secondary arms 42 are squeezed together by pressure of the fingers. In this way, the U-shaped band 12 can be locked in an elongated position for insertion into the mouth.

By locking the orthodontic device 10 in the elongated position, it is easy to position it in the mouth. The U-shaped hooks 16 can be placed behind the last molar and pivoted into position to fit the contour of the last molar on each side of the mouth after which the secondary arms 42 can be unlocked by squeezing them together and allowing the elongated elastic bands 18 to pull the rearwardly extending arms 14 into the hollow channels 24 in telescopic fashion until the U-shaped band exerts pressure on the front teeth proportional to the strength of the elastic bands 18. Since the elastic bands 18 are secured to the studs 32 forming the rivet-like joints between the U-shaped hooks 16 and the elongated slide members 22, the entire device will be held firmly in position within the mouth.

When it is desired to remove the orthodontic device 10 from the mouth, the U-shaped band 12 can be pulled outwardly until the secondary arms 42 are again disposed with the enlarged ends 42b in engagement with the forwardly facing vertical surfaces 38 of the elongated slide members 22. This is facilitated by the forwardly and inwardly ramped surfaces 36 cooperating with the curved surfaces 42d of the enlarged ends 42b which ramp the secondary arms 42 together for passage through the space between the protrusions 34. As a result, the unique cooperation between the secondary arms 42 and the elongated slide members 22 facilitates both insertion and removal of the orthodontic device 10.

As will be appreciated, the biasing force is determined by the strength of the elongated elastic bands 18, so it is possible to control the force applied by the U-shaped band 12. This can be done by substituting elastic bands or springs of different strengths depending upon the amount of force desired. With the unique construction of the present invention, this is easily accomplished by simply detaching the existing elastic bands 18 and replacing them by similar elastic bands 18 of different strength.

In most cases, the front teeth have a normal tendency to protrude forward in which case the orthodontic appliance 10 as illustrated in FIG. 1 is all that is needed to encourage normal teeth positioning. However, when the front teeth have more complex deformity, such as vertical rotation about their axes or rearward displacement, the U-shaped member 20 can be utilized to apply a counterforce.

As can be understood by referring to FIG. 8, the U-shaped member 20 is designed to rest inside the dental arch contiguous to the lingual surface of the front teeth. The curved surface 50 is shaped in the form of a flat arch with the convexity directed forward and oriented transversely flattened in anterior posterior direction. Moreover, the flat arch 50 is sufficiently flexible to adapt to the horizontal contour of the lingual surface of the front teeth when subjected to forward and slightly medial pressure.

As with the inner surface of the U-shaped band 12, the outer surface of the flat arch 50 is grooved and/or ribbed (see FIGS. 5 and 6). This, in effect, prevents skidding against the surface of the teeth and aids in holding the entire orthodontic device 10, including the U-shaped member 20, in position, and may include a plurality of vertical grooves or ribs 66a and/or a plurality of horizontal grooves or ribs 66b or any other means for gripping the teeth. Moreover, since the U-shaped member 20 is articulated, the U-shaped member can be positioned relative to the vertical contour of the posterior surface of the front teeth.

In practice, the spring-loaded cylinder 52c are provided with springs 68 which are always weaker than the biasing force provided by the elongated elastic bands 18. The fact that the rod portion 52d is threaded into the spring-loaded cylinder 52c accommodates increasing or decreasing the total length of the arm 52 and, consequently, changing the amount of forward tension provided. In addition, because of the plunger 52b, there is sufficient axial movement to accommodate insertion of the U-shaped member 20 into the mouth and against the lingual surface of the front teeth.

As shown in FIG. 1, the U-shaped hooks 16 each include a top wall 70 joining the side walls 56 defining the cavities 54. In effect, the cavities are in the form of an inverted U allowing easy separation at their lowest level to admit and engage the studs 60 into the holes 58. Once this has been done, the detents 62, formed of small semi-spheric protrusions, can be disposed in appropriately located indentations or concavities 64 in the walls 56.

In practice, it is preferred to have the U-shaped member 20 mounted with the studs 60 disposed in the holes 58 and with the detents 62 disposed in the lowermost of the indentations or concavities 64 in the walls 56 to facilitate insertion of the device into the mouth. After the U-shaped band 12 has been properly located, the U-shaped member 20 can be moved rearwardly, and then pivoted upwardly until the detents 62 are disposed in the upper indentations or concavities 64 and then allowed to move forwardly into engagement with the lingual surface of the front teeth.

In order to fit most people, the orthodontic appliance 10 can be built in a number of basic sizes. In addition, because of the adjustment features of the present invention, and the variable degree of pressure that can be exerted, several interchangeable springs or elastic bands can be provided. As a result, the orthodontic appliance 10 can be worn as needed to establish and maintain normal alignment of the teeth.

While in the foregoing there has been set forth a preferred embodiment of the invention, it is to be understood that the invention is only to be limited by the spirit and scope of the appended claims.

I claim:

1. An orthodontic appliance, comprising:
   a U-shaped band of flexible material, said band conforming to the labial surface of the dental arch when in position in the mouth, said U-shaped band having a pair of rearwardly extending arms;
   U-shaped anchor means adapted to be releasably secured within the mouth by placement behind a molar on each side of the mouth, said U-shaped anchor means being adapted to maintain said U-shaped band in position against the labial surface of the dental arch;
   resilient means joining said U-shaped anchor means to said arms of said U-shaped band, said resilient means applying a biasing force to the labial surface of the dental arch through said U-shaped band, said biasing force being determined by the strength of said resilient means; and
   means associated with said U-shaped anchor means and said U-shaped band for placing said U-shaped band in a first position resisting the biasing force of said resilient means during placement of said U-shaped anchor means behind a molar on each side of the mouth and a second position transmitting the biasing force of said resilient means to the labial surface of the dental arch through said U-shaped band after placement of said U-shaped anchor means behind a molar on each side of the mouth.

2. The orthodontic appliance as defined by claim 1 wherein said U-shaped anchor means includes a pair of U-shaped hooks, said hooks each facing in a direction opposite the direction said U-shaped band faces and being operatively associated with one of said arms on opposite sides of said U-shaped band, one of said U-shaped hooks being adapted to engage a molar on each side of the mouth.

3. The orthodontic appliance as defined by claim 2 wherein said U-shaped anchor means also includes a pair of elongated slide members, said slide members comprising said means associated with said U-shaped anchor means and said U-shaped band for placing said U-shaped band in said first and second positions and said slide members each having a hollow channel adapted to receive one of said arms of said U-shaped band in telescopic fashion, said U-shaped hooks each being connected to the rearwardmost end of one of said elongated slide members.

4. The orthodontic appliance as defined by claim 3 wherein each of said U-shaped hooks is attached to the corresponding one of said slide members by a joint, said joint accommodating relative pivotal movement of said U-shaped hooks relative to said slide members, said relative pivotal movement permitting said U-shaped hooks to be positioned so as to comfortably and securely engage a molar on each side of the mouth.

5. The orthodontic appliance as defined by claim 3 wherein said resilient means comprises a pair of elongated biasing members, one of said biasing members being associated with each of said arms of said U-shaped band and extending from a point adjacent the rearwardmost end of the corresponding one of said slide members to a point on the corresponding arm forward of said slide member, said biasing members applying a force tending to telescope said arms further into said slide members.

6. The orthodontic appliance as defined by claim 5 wherein said elongated slide members each include a second hollow channel extending parallel to said arm-receiving hollow channel, said second hollow channels being substantially aligned with connection means for said biasing members associated with said arms and said anchor means, said biasing members extending through said second hollow channels of said elongated slide members.

7. The orthodontic appliance as defined by claim 6 wherein said connection means includes a corresponding pair of studs on each of said arms and anchor means, said biasing members comprising elastic bands, said elastic bands joining said corresponding pairs of studs and extending through said second hollow channels of said slide members.

8. The orthodontic appliance as defined by claim 3 wherein said elongated slide members each include a pair of inwardly directed protrusions in said hollow channel defined by forwardly and inwardly ramped surfaces terminating in forwardly facing vertical surfaces, said rearwardly extending arms each being split lengthwise to define a pair of secondary arms adapted to be disposed in locked position against said forwardly facing vertical surfaces during placement of said appliance in the mouth, said secondary arms being adapted to be forced together for insertion past said forwardly facing vertical surfaces after said U-shaped hooks have been placed in engagement with a molar on each side of the mouth.

9. The orthodontic appliance as defined by claim 8 wherein said secondary arms each include a narrow elongated portion terminating in an enlarged end, said enlarged ends each including a rearwardly facing vertical surface adapted to be disposed in engagement with one of said forwardly facing vertical surfaces of said inwardly directed protrusions of said slide members, said enlarged ends also each including a curved surface adapted to cooperate with one of said forwardly and inwardly ramped surfaces of said slide members.

10. The orthodontic appliance as defined by claim 1 wherein said U-shaped band is formed of plastic and includes an embossment simulating teeth on the outer surface thereof.

11. The orthodontic appliance as defined by claim 1 wherein said U-shaped band is formed of plastic and includes a plurality of grooves to grip the teeth on the inner surface thereof.

12. The orthodontic appliance as defined by claim 1 wherein said U-shaped band is formed of plastic, said arms being movable toward one another for insertion of said appliance into the mouth.

13. An orthodontic appliance, comprising:
a U-shaped band of flexible material, said band conforming to the labial surface of the dental arch when in position in the mouth, said U-shaped band having a pair of rearwardly extending arms;
U-shaped anchor means adapted to be releasably secured within the mouth by placement behind a molar on each side of the mouth, said U-shaped anchor means being adapted to maintain said U-shaped band in position against the labial surface of the dental arch;
resilient means joining said U-shaped anchor means to said arms of said U-shaped band, said resilient means applying a biasing force to the labial surface of the dental arch through said U-shaped band, said biasing force being determined by the strength of said resilient means;
means associated with said U-shaped anchor means and said U-shaped band for placing said U-shaped band in a first position resisting the biasing force of said resilient means during placement of said U-shaped anchor means behind a molar on each side of the mouth and a second position transmitting the biasing force of said resilient means to the labial surface of the dental arch after placement of said U-shaped anchor means behind a molar on each side of the mouth;
means for applying a counterforce to the front teeth of the dental arch, said counterforce applying means being releasably securable to said U-shaped anchor means; and
means associated with said U-shaped anchor means and said counterforce applying means for placing said counterforce applying means in a first position remote from the front teeth of the dental arch during placement of said U-shaped anchor means behind a molar on each side of the mouth and a second position in engagement with the front teeth of the dental arch after placement of said U-shaped anchor means behind a molar on each side of the mouth.

14. The orthodontic appliance as defined by claim 13 wherein said counterforce applying means is a generally U-shaped member adapted to fit within said U-shaped band, said U-shaped member having a curved surface adapted to engage the posterior surface of the front teeth and a pair of connecting arms extending therefrom, said connecting arms being adapted to be releasably secured to said U-shaped anchor means and comprising said means associated with said U-shaped anchor means and said counterforce applying means for placing said counterforce applying means in said first and second positions.

15. The orthodontic appliance as defined by claim 14 wherein said connecting arms each include intermediate biasing means, said biasing means comprising a first arm portion having a plunger disposed in one end of a spring loaded cylinder and a second arm portion threaded into the other end of said cylinder, said connecting arms biasing said U-shaped member outwardly to provide said counterforce.

16. The orthodontic appliance as defined by claim 15 wherein said resilient means comprises a pair of elongated biasing members, one of said biasing members being associated with each of said arms of said U-shaped band and extending from a point adjacent the rearward-most end of the corresponding one of said slide members to a point on the corresponding arm forward of said slide member, said biasing members applying a force tending to telescope said arms further into said slide members.

17. The orthodontic appliance as defined by claim 16 wherein said elongated slide members each include a second hollow channel extending parallel to said arm-receiving hollow channel, said second hollow channels being substantially aligned with connection means for said biasing members associated with said arms and said anchor means, said biasing members extending through said second hollow channels of said elongated slide members.

18. The orthodontic appliance as defined by claim 14 wherein said U-shaped band is formed of plastic and includes a plurality of grooves to grip the teeth on the inner surface thereof, said arms of said U-shaped band being movable toward one another for insertion of said appliance into the mouth, said U-shaped member also having a plurality of grooves to grip the teeth on the outer surface thereof.

19. The orthodontic appliance as defined by claim 13 wherein said U-shaped anchor means includes a pair of U-shaped hooks, said hooks each facing in a direction opposite the direction said U-shaped band faces and being opperatively associated with one of said arms on opposite sides of said U-shaped band, one of said U-shaped hooks being adapted to engage a molar on each side of the mouth.

20. The orthodontic appliance as defined by claim 19 wherein said U-shaped anchor means also includes a pair of elongated slide members, said slide members comprising said means associated with said U-shaped anchor means and said U-shaped band for placing said U-shaped band in said first and second positions and said slide members each having a hollow channel adapted to receive one of said arms of said U-shaped band in telescopic fashion, said U-shaped hooks each being connected to the rearwardmost end of one of said elongated slide members.

21. The orthodontic appliance as defined by claim 20 wherein each of said U-shaped hooks is attached to the corresponding one of said slide members by a joint, said joint accommodating relative pivotal movement of said U-shaped hooks relative to said slide members, said relative pivotal movement permitting said U-shaped hooks to be positioned so as to comfortably and securely engage a molar on each side of the mouth.

22. The orthodontic appliance as defined by claim 21 wherein said U-shaped hooks each include a forwardly facing cavity formed by a pair of generally parallel walls, said cavities being adapted to receive said connecting arms, said connecting arms and walls having mutually interengageable connection means.

23. The orthodontic appliance as defined by claim 22 wherein said connection means includes a pair of aligned stud receiving holes in each of said pairs of walls defining said cavities, said connecting arms each having a pair of oppositely facing studs adapted to be releasably disposed in one of said pairs of holes, said U-shaped member being pivotable about said studs.

24. The orthodontic appliance as defined by claim 23 wherein said connecting means further includes detent means associated with said walls and said connecting arms, said detent means accommodating retention of said U-shaped member in positions of angular adjustment relative to said studs.

25. The orthodontic appliance as defined by claim 24 wherein said detent means includes a detent on each of said connecting arms forwardly of said studs and at least two generally vertically aligned detent receiving indentations forwardly of said holes in each of said pairs of walls.

* * * * *